United States Patent [19]

Zasloff

[11] Patent Number: 5,073,542
[45] Date of Patent: Dec. 17, 1991

[54] CPF PEPTIDE COMPOSITIONS AND THEIR USE IN INHIBITING GROWTH OF TARGET CELLS OR A VIRUS

[75] Inventor: Michael Zasloff, Merion Station, Pa.

[73] Assignee: Magainin Sciences Inc., Plymouth Meeting, Pa.

[21] Appl. No.: 462,012

[22] Filed: Jan. 8, 1990

Related U.S. Application Data

[63] Continuation-in-part of Ser. No. 362,689, Jun. 7, 1989, abandoned, which is a continuation-in-part of Ser. No. 260,861, Oct. 21, 1988, abandoned.

[51] Int. Cl.$^5$ .......................... A61K 37/02; C07K 7/10
[52] U.S. Cl. .......................................... 514/12; 514/13; 514/14; 530/324; 530/325; 530/326
[58] Field of Search .............................. 514/12, 13, 14; 530/324, 325, 326

[56] References Cited

U.S. PATENT DOCUMENTS 4,507,230 3/1985 Tam et al. .......................... 530/334

OTHER PUBLICATIONS

Gibson et al., *J. Biol. Chem.*, vol. 261, No. 12, pp. 5341–5349 (1986).
Vlasak et al., *Eur. J. Biochem.*, vol. 169, pp. 53–58 (1987).

*Primary Examiner*—Lester L. Lee
*Attorney, Agent, or Firm*—Elliot M. Olstein; Raymond J. Lillie

[57] ABSTRACT

CPF peptides and/or analogues or derivatives are used as a pharmaceutical. Such peptides have antibiotic and/or anti-viral and/or anti-tumor and/or anti-spermicidal activity.

15 Claims, No Drawings

CPF PEPTIDE COMPOSITIONS AND THEIR USE IN INHIBITING GROWTH OF TARGET CELLS OR A VIRUS

This Application is a continuation-in-part of application Ser. No. 362,689, filed June 7, 1989, now abandoned, which is a continuation-in-part of application Ser. No. 260,861, filed Oct. 21, 1988, now abandoned.

The present invention as related to the use of certain peptides and to compositions containing such peptides. More particularly, the present invention is directed to pharmaceutical uses and compositions of certain peptides known as CPF peptides and analogues and derivatives thereof.

Some of the CPF peptides which are used in the present invention have been described in the literature and comprise the following sequences:

(1) GFGSFLGLALKAALKIGANALGGAPQQ
(2) GLASFLGKALKAGLKIGAHLLGGAPQQ
(3) GLASLLGKALKAGLKIGTHFLGGAPQQ
(4) GLASLLGKALKATLKIGTHFLGGAPQQ
(5) GFASFLGKALKAALKIGANMLGGTPQQ
(6) GFGSFLGKALKAALKIGANALGGAPQQ
(7) GFGSFLGKALKAALKIGANALGGSPQQ
(8) GFASFLGKALKAALKIGANLLGGPTQQ

The above is expressed as single letter code for amino acids.

A review of the CPF peptides can be found in Richter K. Egger, R., and Kreil (1986) J. Biol. Chem 261, 3676–3680; Wakabayashi, T., Kato, H., and Tachibaba, S. (1985) Nucleic Acids Research 13, 1817–1828; Gibson, B. W., Poulter, L., Williams, D. H., and Maggio, J. E. (1986) J. Biol. Chem 261, 5341–5349.

It should be noted that no function has been ascribed to these peptides in prior published reports. Indeed, Kreil et al state in a recent paper: "At present it is not known whether these peptides have any biological activity." (Vlasak, R., Wiborg, O., Richter, K., Burgschwaiger, J. V., and Kreil, G., (1987) Eur. J. Bichem. 169, p. 53).

In accordance with one aspect of the present invention, there is provided a composition comprised of CPF peptides and/or biologically active analogues or derivatives thereof and a pharmaceutical carrier.

In accordance with another aspect of the present invention, there is provided a process wherein a CPF peptide and/or biologically active analogue or derivative thereof is administered to inhibit growth of a target cell or cells.

The terms analogue and/or derivative encompasses peptides having more or less amino acids than the CPF peptides and one or more changes in the amino acids of the CPF peptide.

CPF peptides as well as analogues and derivatives thereof are herein sometimes referred to collectively as CPF peptides.

The CPF peptide is preferably one which includes the following basic peptide structure x:

$$-R_1-R_1-R_2-R_2-R_1-R_1-R_3-R_1-R_1-R_1-R_3-R_1-R_1-R_4-R_5-R_1-$$

wherein
$R_1$ is a hydrophobic amino acid;
$R_2$ is a hydrophobic amino acid or a basic hydrophilic amino acid;
$R_3$ is a basic hydrophilic amino acid;
$R_4$ is a hydrophobic or neutral hydrophilic amino acid; and
$R_5$ is a basic or neutral hydrophilic amino acid.

The hereinabove basic structure is hereinafter symbolically indicated as X.

The hydrophobic amino acids are Ala, Cys, Phe, Gly, Ile, Leu, Met, Val, Trp, and Tyr.

The neutral hydrophilic amino acids are Asn, Gln, Ser, and Thr.

The basic hydrophilic amino acids are Lys, Arg, His, and ornithine (o).

The CPF peptide may include only the hereinabove noted amino acids or may include additional amino acids at the amino and/or carboxyl end or both the amino and carboxyl end. In general, the peptide does not include more than 40 amino acids.

The CPF peptides including the above basic structure preferably have from 1 to 4 additional amino acids at the amino end.

Accordingly, such preferred peptides may be represented by the structural formula:

$$Y-X-$$

wherein X is the hereinabove described basic peptide structure and Y is
(i) $R_5-$, or
(ii) $R_2-R_5-$; or
(iii) $R_1-R_2-R_5$; or
(iv) $R_2-R_1-R_2-R_5$; preferably Glycine—$R_1$—$R_2$—$R_5$.
wherein $R_1$, $R_2$ and $R_5$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

$$-X-Z$$

wherein X is the hereinabove defined basic peptide structure and Z is
(i) $R_1-$, or
(ii) $R_1-R_1-$; or
(iii) $R_1-R_1-R_4$; or
(iv) $R_1-R_1-R_4-R_4$; or
(v) $R_1-R_1-R_4-R_4-R_6$; or
(vi) $R_1-R_1-R_4-R_4-R_6-$Gln; or
(vii) $R_1-R_1-R_4-R_4-R_6-$Gln—Gln, wherein $R_1$ and $R_4$ are as previously defined, and $R_6$ is proline or a hydrophobic amino acid.

Preferred peptides may be represented by the following structural formula $$(Y)_a-X-(Z)_b$$

wherein X, Y and Z are as previously defined and a is 0 or 1 and b is 0 or 1.

As representative examples of CPF like peptides used in the present invention, there may be mentioned peptides represented by the following (single letter amino acid code):

G12S3LG4ALKA5LKIG678LGG9(10)QQ

Where:
1 = F, L

2=G, A
3=F, L
4=K, L
5=A, G, T
6=A, T
7=H, N
8=A, M, F, L
9=A, S, T
10=P, L

The numbered amino acids may be employed as described in any combination to provide either a basic CPF peptide structure or an analogue or derivative thereof.

The CPF peptides and/or analogues and/or derivatives thereof are ion channel forming peptides. An ion channel forming peptide or ionophore is one which increases the permeability for ions across a natural or synthetic lipid membrane. Christensen et al. PNAS Vol. 85 P. 5072-76 (July 1988) describes methodology which indicates whether or not a peptide has ion channel properties and is therefore an ionophore. As used herein an ion channel-forming peptide is a peptide which has ion channel-forming properties as determined by the method of Christensen, et al.

In general, the CPF peptides and/or analogues or derivatives thereof are generally water soluble to a concentration of at least 20 mg/ml at neutral pH in water. In addition, such peptides are non-hemolytic; i.e., they will not rupture blood cells at effective concentrations. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

The CPF peptides and/or analogues or derivatives thereof may be administered to a host; for example a human or non-human animal, in an amount effective to inhibit growth of a target cell. Thus, for example, the CPF peptides and/or analogues or derivatives thereof may be used as antimicrobial agents anti-viral agents, antibiotics, anti-tumor agents, spermicides, as well as exhibiting other bioactive functions.

The term "antimicrobial" as used herein means that the polypeptides of in the present invention inhibit, prevent, or destroy the growth or proliferation of microbes such as bacteria, fungi, viruses, or the like.

The term "antibiotic" as used herein means that the polypeptides employed in the present invention produce effects adverse to the normal biological functions of the cell, tissue, or organism including death or destruction and prevention of the growth or proliferation of the biological system when contacted with the polypeptides.

The term "spermicidal" as used herein means that the polypeptides employed in the present invention, inhibit, prevent, or destroy the motility of sperm.

The term "antiviral" as used herein means that the polypeptides employed in the present invention inhibit, prevent, or destroy the growth or proliferation of viruses.

The term anti-tumor as used herein means that the polypeptide inhibits the growth of or destroys tumors.

The polypeptides of the present invention have a broad range of potent antibiotic activity against a plurality of microorganisms including gram-positive and gram-negative bacteria, fungi, protozoa, and the like. The polypeptides of the present invention allow a method for treating or controlling microbial infection caused by organisms which are sensitive to the polypeptides. Such treatment may comprise administering to a host organism or tissue susceptible to or affiliated with a microbial infection an antimicrobial amount of at least one of the polypeptides.

Because of the antibiotic properties of the polypeptides, they may also be used as preservatives or sterilants of materials susceptible to microbial contamination.

The CPF peptide and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The polypeptide compositions may also be used in combination with adjuvants, protease inhibitors, or compatible drugs where such a combination is seen to be desirable or advantageous in controlling infection caused by harmful microorganisms including protozoa viruses, and the like.

The peptide(s) of the present invention may be administered to a host; in particular an animal, in an effective antibiotic and/or anti-tumor and/or anti-viral and/or anti-microbial and/or an antispermicidal amount.

Depending on the use, a composition in accordance with the invention will contain an effective antimicrobial amount and/or an effective antispermicidal amount and/or an effective anti-viral amount and/or an effective anti-tumor amount and/or an effective antibiotic amount of one or more of the hereinabove described peptides which have such activity.

The peptides, when used in topical compositions, are generally present in an amount of at least 0.1%, by weight. In most cases, it is not necessary to employ the peptide in an amount greater than 1.0%, by weight.

In employing such compositions systemically (intramuscular, intravenous, intraperitoneal), the active peptide is present in an amount to achieve a serum level of the peptide of at least about 5 ug/ml. In general, the serum level of peptide need not exceed 500 ug/ml. A preferred serum level is about 100 ug/ml. Such serum levels may be achieved by incorporating the peptide in a composition to be administered systemically at a dose of from 1 to about 10 mg/kg. In general, the peptide(s) need not be administered at a dose exceeding 100 mg/kg.

The present invention will be further described with respect to the following examples; however, the scope of the invention is not to be limited thereby:

TABLE I demonstrates the antibacterial activity of the peptide GFGSFLGLALKAALKIGANALGGAPQQ [CPF (I)] and the peptide GFASFLGKALKAALKIGANLLGGTPQQ [CPF (II)].

TABLE II shows the minimal inhibitory concentrations of CPF (I) and CPF (II) against several strains of bacteria and fungi.

TABLE III lists the minimal effective concentrations of CPF (I) and CPF (II) necessary to physically disrupt several different species of protozoa. In each case the peptide induces osmotic swelling.

TABLE I

| Peptide | Antibacterial Activity of Peptides<br>Zone of Inhibition on Lawn of<br>E. coli (50 ug of peptide) (mm) |
|---|---|
| CPF (I) | 15 |
| CPF (II) | 15 |

TABLE II
SPECTRUM OF ANTI-MICROBIAL ACTIVITY OF SYNTHETIC PEPTIDES

| ORGANISM | MINIMAL INHIBITORY CONCENTRATION (ug/ml) | |
|---|---|---|
| | CPF (I) | CPF (II) |
| E. coli | 10–50 | 10–50 |
| P. aeruginosa | 50–100 | 50–100 |
| S. pyogenes | 100–200 | 100–200 |
| S. cerevisiae | 100–200 | 100–200 |
| C. albicans | 50–100 | 50–100 |

TABLE III
SENSITIVITY OF PROTOZOA TO SYNTHETIC PEPTIDES
Minimal Disruptive Concentration (ug/ml)

| | CPF (I) | CPF (II) |
|---|---|---|
| P. caudatum | 10 | 10 |
| T. pyriformis | 10 | 10 |
| A. casteliani | 2 | 2 |

TABLE IV
ACTIVITY AGAINST MALIGNANT CELLS (ug/ml)

| | CPF (I) | CPF (II) |
|---|---|---|
| Vero cells | 250 | 250 |
| Ehrlich Ascites | 250 | 250 |

(Legend) Cells were grown in MEM with 10% fetal calf serum. Peptide was added directly to a well containing a confluent lawn of cells and incubated at 37° C. for 30 min. The concentration at which greater than 90% of the cells were killed as determined by permeabilization to Trypan Blue is noted.

Table V shows the minimal inhibitory concentrations of CPF (II) against six different species of fungi:

TABLE V
MIC VALUES OF CPF (II) AGAINST FUNGI

| Fungus | MIC (mg/ml) |
|---|---|
| Microsporum canis | 31 |
| Trichophyton rubrum | 62 |
| Trichophyton mentagrophytes | 31 |
| Candida albicans | 8 |
| Saccharomyces Cerevisiae | 16 |
| Cryptococcus neoformans | 2 |

(Legend) Either trypticase soy broth, half-strength, or supplemented yeast nitrogen base is used as a nutrient source. The supplemented yeast mitrogen base is prepared by adding yeast nitrogen base without amino acids plus 6.7 g ammonium sulfate (Difco), 10.0 g D-glucose, and 1.5 g L-asparagine to 100 ml of distilled water. The pH is adjusted to 5.5 with the addition of 1N NaOH and the solution is filter sterilized through a 0.2µ (pore size) filter and stored at 4° C. 15 ml of the supplemented yeast nitrogen base is heated to 50° C. together with 135 ml of 0.01M sodium phosphate buffer (pH 7.0) and added to 50 ml of sterile molten agarose (2% w/v). After mixing, 4.5 ml of the molten medium is added to 0.5 ml of the peptide solution. The final concentration of medium components is as follows:

yeast nitrogen base: 0.45% (w/v)
glucose: 0.67% (w/v)
L-asparagine: 0.1% (w/v)
sodium phosphate: 61 mM
agarose: 0.5% (w/v)
The final pH is 6.5.

The half-strength trypticase soy agarose is prepared as follows: 15 g of tryptic soy broth (Difco), and 10 g of D-glucose are added to 100 ml of distilled water. This mixture is filtered, sterilized through a 0.45 µm (pore size) filter and stored at room temperature. For preparation of the final medium, the tryptic soy broth is mixed with 0.01M sodium phosphate buffer (pH 7.0) and 2% molten agarose are added in the same proportions as indicated for the preparation of the supplemented yeast nitrogen base. Peptide solution is then added, also as hereinabove described.

The appropriate species of fungi are inoculated on agarose plates containing 1% (w/v) yeast extract, 2% (w/v) peptone, 2% (w/v) agarose, and incubated at 37° C. for 24–48 hours. When the assay is to be carried out, a sample of fungus is taken from the plate and diluted in autoclaved deionized distilled water to a concentration of $2 \times 10^7$ cells/ml or $2 \times 10^7$ spores/ml (as determined by a hemacytometer). 5 ml of these suspensions are used for the inoculations.

Stock solutions of the peptide are prepared by dissolving the peptide in autoclaved deionized distilled water at a concentration of 5.0 mg/ml. When the assay is to be carried out, working solutions of the peptide are prepared by performing serial dilutions (1:2) in sterile test tubes, using autoclaved deionized distilled water to give concentrations from 5.0 µg/ml to 5 mg/ml. Then 0.5 ml of these solutions are added to the molten agarose medium, as described above, to give final concentrations of 0.5 mg/ml to 0.5 µg/ml.

Into each well of a 24-well polystyrene plate, 1 ml of peptide-media in the various concentrations is dispensed and allowed to cool. Each well of the plate is inoculated with 5.0 ml of fungi. The plates are incubated at 30° C. for 24–48 hours. The MIC is evaluated by eye and is defined as the lowest concentration of peptide that permits no visible growth in the well.

Table VI shows the IC$_{50}$ values of CPF(II) against various human tumor cell lines.

TABLE VI
IC$_{50}$ VALUES OF CPF (II) AGAINST HUMAN TUMOR CELL LINES

| Cell Line | IC 50 (ug/ml) |
|---|---|
| Melanoma (SK-MEL-1) | 52 |
| Lymphoma (Daudi) | 107 |
| Leukemia (CCRF-CEM) | 33 |
| Colon (Colo-3208M) | 68 |
| Small Cell Lung Carcinoma (H69) | 23 |
| Non-small lung Carcinoma (H22) | 20 |
| Squamus Cell Lung Carcinoma (SK-MES-1) | 20 |

(Legend) Cell lines are grown in RPMI 1640 with 9% fetal bovine serum, 1% iron-supplemented calf serum, 2 mM L-glutamine, and 50 μg/ml gentamicin, at 37° C. in 5% $CO_2$ with 95% humidity. For each assay, the cells are plated in 96 well plastes and grown for 48 hours to allow them to recover from passaging and attain the desired cell density. The peptide is then diluted in complete media and added to the cells at concentrations from 0 to 500 μg/ml. The plates are then incubated for 24 hours and then assayed for cytotoxicity using a vital dye conversion assay. Scudiero, et al, *Cancer Res.*, 48:4827–4833 (1988). From the cytotoxicity data, $IC_{50}$ values are calculated for CPF (II) against each cell line. $IC_{50}$ is defined as the dose to reduce the viable cell number by 50%.

Numerous modifications and variations of the present invention are possible in light of the above teachings; therefore, within the scope of the appended claims the invention may be practiced otherwise than as particularly described.

What is claimed is:

1. A composition for inhibiting the growth of a target cell or virus, comprising:

a CPF peptide and a pharmaceutical carrier, said CPF peptide being present in an amount effective to inhibit growth of a target cell or virus, said CPF peptide having the following structure:

$(Y)_a-X-(Z)_b$, wherein X has the following structure:

$R_1-R_1-R_2-R_2-R_1-R_1-R_3-R_1-R_1-R_1-R_3-R_1-R_1-R_4-R_5-R_1$,

Y is:
   (i) $R_5$;
   (ii) $R_2-R_5$;
   (iii) $R_1-R_2-R_5$; or
   (iv) $R_2-R_1-R_2-R_5$, and
   Z is:
   (i) $R_1$;
   (ii) $R_1-R_1$;
   (iii) $R_1-R_1-R_4$;
   (iv) $R_1-R_1-R_4-R_4$;
   (v) $R_1-R_1-R_4-R_4-R_6$;
   (vi) $R_1-R_1-R_4-R_4-R_6-Gln$; or
   (vii) $R_1-R_1-R_4-R_4-R_6-Gln-Gln$, wherein
   $R_1$ is a hydrophobic amino acid;
   $R_2$ is a basic hydrophilic amino acid or a hydrophobic amino acid; $R_3$ is a basic hydrophilic amino acid; $R_4$ is a hydrophobic or neutral hydrophilic amino acid; $R_5$ is a basic hydrophilic or neutral hydrophilic amino acid; $R_6$ is proline or a hydrophobic amino acid, a is 0 or 1, and b is 0 or 1.

2. A process for inhibiting the growth of a target cell or virus in a host, comprising:

administering to a host a CPF peptide in an amount effective to inhibit growth of a target cell or virus in a host, said CPF peptide having the following structural formula:

$(Y)_a-X-(Z)_b$, wherein X has the following structure:

$R_1-R_1-R_2-R_2-R_1-R_1-R_3-R_1-R_1-R_1-R_3-R_1-R_1-R_4-R_5-R_1$;

Y is:
   (i) $R_5$;
   (ii) $R_2-R_5$;
   (iii) $R_1-R_2-R_5$; or
   (iv) $R_2-R_1-R_2-R_5$, and
   Z is:
   (i) $R_1$;
   (ii) $R_1-R_1$;
   (iii) $R_1-R_1-R_4$;
   (iv) $R_1-R_1-R_4-R_4$;
   (v) $R_1-R_1-R_4-R_4-R_6$;
   (vi) $R_1-R_1-R_4-R_4-R_6-Gln$; or
   (vii) $R_1-R_1-R_4-R_4-R_6-Gln-Gln$,
   wherein $R_1$ is a hydrophobic amino acid; $R_2$ is a basic hydrophilic amino acid or hydrophobic amino acid; $R_3$ is a basic hydrophilic amino acid; $R_4$ is a hydrophobic or neutral hydrophilic amino acid; $R_5$ is a basic hydrophilic amino acid or neutral hydrophilic amino acid; $R_6$ is proline or a hydrophobic amino acid; a is 0 or 1, and b is 0 or 1.

3. A process for inhibiting growth of a target cell in a material susceptible to microbial contamination, comprising:

administering to said material susceptible to microbial contamination a CPF peptide in an amount effective to inhibit growth of a target cell in said material susceptible to microbial contamination, said CPF peptide having the following structure:

$(Y)_a-X-(Z)_b$, wherein X has the following structure:

$R_1-R_1-R_2-R_2-R_1-R_1-R_3-R_1-R_1-R_1-R_3-R_1-R_1-R_4-R_5-R_1$;

Y is:
   (i) $R_5$;
   (ii) $R_2-R_5$;
   (iii) $R_1-R_2-R_5$; or
   (iv) $R_2-R_1-R_2-R_5$; and
   Z is:
   (i) $R_1$;
   (ii) $R_1-R_1$;
   (iii) $R_1-R_1-R_4$;
   (iv) $R_1-R_1-R_4-R_4$;
   (v) $R_1-R_1-R_4-R_4-R_6$;
   (vi) $R_1-R_1-R_4-R_4-R_6-Gln$; or
   (vii) $R_1-R_1-R_4-R_4-R_6-Gln-Gln$, wherein
   $R_1$ is a hydrophobic amino acid; $R_2$ is a basic hydrophilic amino acid or a hydrophobic amino acid; $R_3$ is a basic hydrophilic amino acid; $R_4$ is a hydrophobic or neutral hydrophilic amino acid; $R_5$ is a basic hydrophilic amino acid or neutral hydrophilic amino acid; $R_6$ is a proline or a hydrophobic amino acid, a is 0 or 1, and b is 0 or 1.

4. The composition of claim 1 wherein the peptide has the following structure:

G12S3LG4ALKA5LKIG678LGG9(10)QQ

Where:
   1 = F, L
   2 = G, A
   3 = F, L
   4 = K, L
   5 = A, G, T
   6 = A, T
   7 = H, N
   8 = A, M, F, L
   9 = A, S, T

10=P, L

5. The process of claim 2 wherein said administering is to an animal host in an effective anti-tumor amount.

6. The process of claim 2 wherein said administering is to an animal host in an effective anti-viral amount.

7. The process of claim 2 wherein said administering is to an animal host in an effective antimicrobial amount.

8. The process of claim 2 wherein said administering is to an animal host in an effective antibiotic amount.

9. The process of claim 2 wherein said administering is to an animal host in an effective anti-spermicidal amount.

10. The composition of claim 1 wherein the peptide is of the following structural formula as defined by the single letter amino acid code:

GFGSFLGLALKAALKIGANALGGAPQQ.

11. The composition of claim 1 wherein the peptide is of the following structural formula as defined by the single letter amino acid code:

GFASFLGKALKAALKIGANLLGGTPQQ.

12. The process of claim 2 wherein the peptide is of the following structural formula as defined by the single letter amino acid code:

GFGSFLGLALKAALKIGANALGGAPQQ.

13. The process of claim 2 wherein the peptide is of the following structural formula as defined by the single letter amino acid code:

GFASFLGKALKAALKIGANLLGGTPQQ.

14. The process of claim 2 wherein said CPF peptide is administered topically.

15. The process of claim 2 wherein said CPF peptide is administered systemically.

* * * * *